United States Patent [19]

Hrebeniuk

[11] Patent Number: Plant 6,491

[45] Date of Patent: Dec. 27, 1988

[54] POINSETTIA PLANT NAMED H-365

[76] Inventor: Alexander Hrebeniuk, Rd. #1, Box 118, Sugar Run, Pa. 18846

[21] Appl. No.: 42,032

[22] Filed: Apr. 24, 1987

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Evans

[57] ABSTRACT

A Poinsettia plant named H-365, characterized by its bright red bracts; upright and compact growth habit, with excellent branching and breaking; 8½ week flowering response; excellent growth and flowering under cool conditions; excellent keeping qualities; cyathias which remain up to five weeks after blooming.

1 Drawing Sheet

1

The present invention relates to a new and distinct cultivar of poinsettia plant known by the cultivar name H-365, and botanically known as *Euphorbia pulcherrima.*

H-365 is a product of a planned breeding program which had the objective of creating new poinsettia cultivars with long lasting blooms, excellent keeping quality, bright red bract color, free branching, and the ability to respond well under cool growing conditions. Such traits in combination were not present or needed improvements in previously available commercial cultivars.

H-365 was originated by applicant from a hybridization made in a controlled breeding program in Sugar Run, Pa. in 1984. The female parent was HL-1 Red, a cultivar of applicant disclosed in U.S. Plant Pat. No. 4,434. The male parent of H-365 was Annette Hegg Dark Red, disclosed in U.S. Plant Pat. No. 3,160. H-365 was discovered and selected as one flowing plant within the progeny of the stated parentage by applicant in December 1984 in a controlled environment in Sugar Run, Pa.

The first act of asexual reproduction of H-365 was accomplished when vegetative cuttings were taken from the initial selection in April 1985 in a controlled environment in Sugar Run, Pa. by a technician working under formulations established and supervised by applicant. Horticultural examination of selected units initiated in December 1985 has demonstrated that the combination of characteristics as herein disclosed for H-365 are firmly fixed and are retained through successive generations of asexual reproduction.

H-365 has not been observed under all possible environmental conditions. The phenotype may vary significantly with variations in environment such as temperature, light intensity, and day length. The following observations, measurements and comparisons describe plants grown in Sugar Run and Parkerford, Pa. under greenhouse conditions which approximate those generally used in commercial practice.

The following traits have been repeatedly observed and are determined to be basic characteristics of H-365 which in combination distinguish this Poinsettia as a new and distinct cultivar:

1. Eight-and-one-half week flowering response under black cloth.
2. Upright and compact growth habit, and very freely branching.

2

3. Six to eight breaks per pinch average.
4. Breaks very strongly, attached to main stem, not breaking off easily, which makes this variety excellent for shipping.
5. Excellent keeping qualities; does not drop leaves easily and holds bright red bract color very well (fade resistant).
6. Stems of plant are green, leaf petroles are red and leaves are green.
7. Performs well as a pinched or non-pinched plant.
8. Grows and flowers well under cool growing conditions.
9. Cyathia remain on plant very long after bloom, up to five weeks.

The accompanying photographic drawing shows typical inflorescence and foliage characteristics of H-365, with colors being as nearly true as possible with illustrations of this type. Sheet 1 is a black and white photograph comprising a perspective view of the new cultivar, with certain leaves, bracts and cyathia being colored to depict true color values.

In the following description color references are made to The Royal Horticultural Society Colour Chart. The color values were determined at approximately 2:00 p.m. on Jan. 15, 1987 under fluorescent light at Bradenton, Fla.

Classification:

*Botanical.*—*Euphorbia pulcherrima,* c.v. H-365.

*Commercial.*—Poinsettia.

Parentage:

*Male parent.*—Annette Hegg Dark Red.

*Female parent.*—HL-1 Red.

Plant description:

(A) *Form.*—Double.

(B) *Growth habit.*—Upright and compact, very freely branching after being pinched. Very strong breaking, with an average of six to eight breaks per pinch. Grows and flowers well under cool conditions.

(C) *Rooting.*—Fast, with few problems.

(D) *Blooming season.*—Normally November 15th through December 10th.

(E) *Blooming habit.*—Medium-large bracts develop in treble rows. Keeping quality is excellent, with the bright red bract color being relatively resistant to fade.

Foliage:

(A) *Size.*—From 5 cm wide and 7 cm long up to 11 cm wide and 15 cm long.

(B) *Quantity.*—Up to 16 leaves per flowering stem depending upon culture; long lasting.

(C) *Color.*—New foliage: Upper side: 137A. Under side: 137C. Old foliage: Upper side: 139A. Under side: 139B. Leaf petiole: 146A.

(D) *Shape.*—Leaves ovate, apex acuminate, margins ranging from repand to crenate.

(E) *Texture.*—Upper side: velvety. Under side: veins prominent, velvety between veins.

(F) *Edge of margin.*—Slightly wavy to slightly pointed.

(G) *Aspect.*—Pointed.

(H) *Disease resistance.*—Very resistant to botrytis.

Flowers:

(A) *Borne.*—In a compound corymb.

(B) *Quantity.*—No more than 20 per stem, each flower having a nectary.

Bracts:

(A) *Size.*—From 2 cm wide by 4.5 cm long, up to 8 cm wide by 14 cm long on a pinched plant.

(B) *Color.*—53C.

(C) *Cyathia.*—Approximately 12A-B when mature; remain on plant up to five weeks after blooming.

Reproductive organs: Typical Poinsettia, insignificant.

I claim:

1. A new and distinct cultivar of Poinsettia plant named H-365, as described and illustrated, and particularly characterized by its bright red bracts; upright and compact growth habit, with excellent branching and breaking; 8½ week flowering response; excellent growth and flowering under cool conditions; excellent keeping qualities, and by its cyathias which remain up to five weeks after blooming.

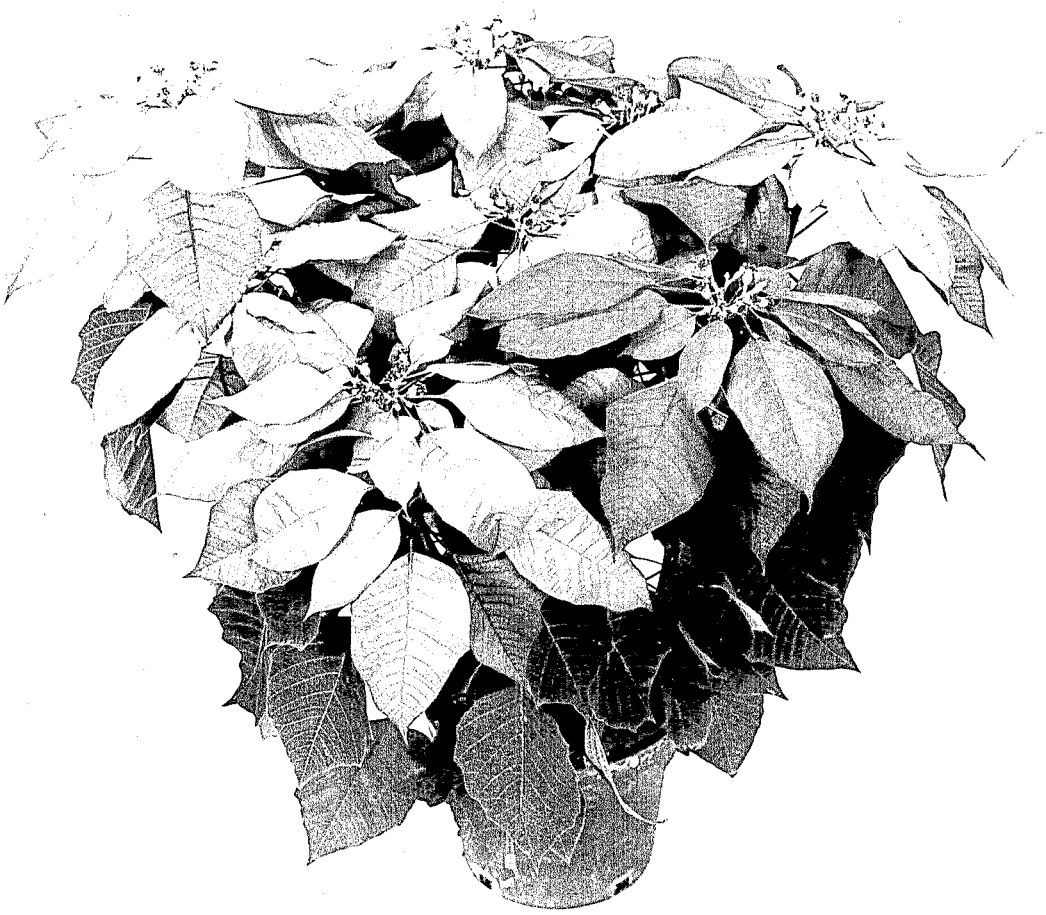

* * * * *